United States Patent [19]
Alden et al.

[11] Patent Number: 5,741,287
[45] Date of Patent: Apr. 21, 1998

[54] SURGICAL TUBULAR CUTTER HAVING A TAPERING CUTTING CHAMBER

[75] Inventors: Donald L. Alden, Sunnyvale; Jeffrey J. Christian, San Jose, both of Calif.

[73] Assignee: Femrx, Inc., Sunnyvale, Calif.

[21] Appl. No.: 746,541

[22] Filed: Nov. 13, 1996

Related U.S. Application Data

[60] Provisional application No. 60/029,537 Nov. 1, 1996.

[51] Int. Cl.$^6$ .............................. A61B 17/32; A61B 17/20
[52] U.S. Cl. .............................. 606/170; 606/167; 604/22
[58] Field of Search .............................. 604/19, 22, 35; 606/167, 107, 171, 180, 187, 170

[56] References Cited

U.S. PATENT DOCUMENTS

| | | | |
|---|---|---|---|
| 1,493,240 | 5/1924 | Bohn. | |
| 4,646,738 | 3/1987 | Trott. | |
| 4,787,889 | 11/1988 | Steppe et al. | 604/22 |
| 4,850,354 | 7/1989 | Burleson et al. | 606/180 |
| 5,061,238 | 10/1991 | Shuler | 604/22 |
| 5,160,318 | 11/1992 | Shuler | 604/22 |
| 5,217,479 | 6/1993 | Shuler | 606/180 |
| 5,269,798 | 12/1993 | Winkler | 606/170 |
| 5,364,395 | 11/1994 | West, Jr. | 606/46 |
| 5,383,884 | 1/1995 | Summers | 606/170 |
| 5,437,630 | 8/1995 | Daniel et al. | 604/22 |
| 5,601,583 | 2/1997 | Donahue et al. | 606/180 |

*Primary Examiner*—Glenn K. Dawson
*Attorney, Agent, or Firm*—Townsend and Townsend and Crew LLP

[57] ABSTRACT

The invention provides tubular surgical cutters having conical or tapering cutting chambers along substantially the entire length of their cutting apertures. Tissues which are drawn into such a conical chamber and severed from the adjacent tissue are quite easily drawn proximally for aspiration, substantially reducing the likelihood that they will clog the cutter mechanism. In some embodiments, an inner cutting tube having an orifice which is smaller than that of the outer cutting tube limits the size of tissue fragments entrained within the cutting chamber, further reducing the possibility that those fragments will clog the aspiration lumen and interrupt the tissue removal process.

15 Claims, 3 Drawing Sheets

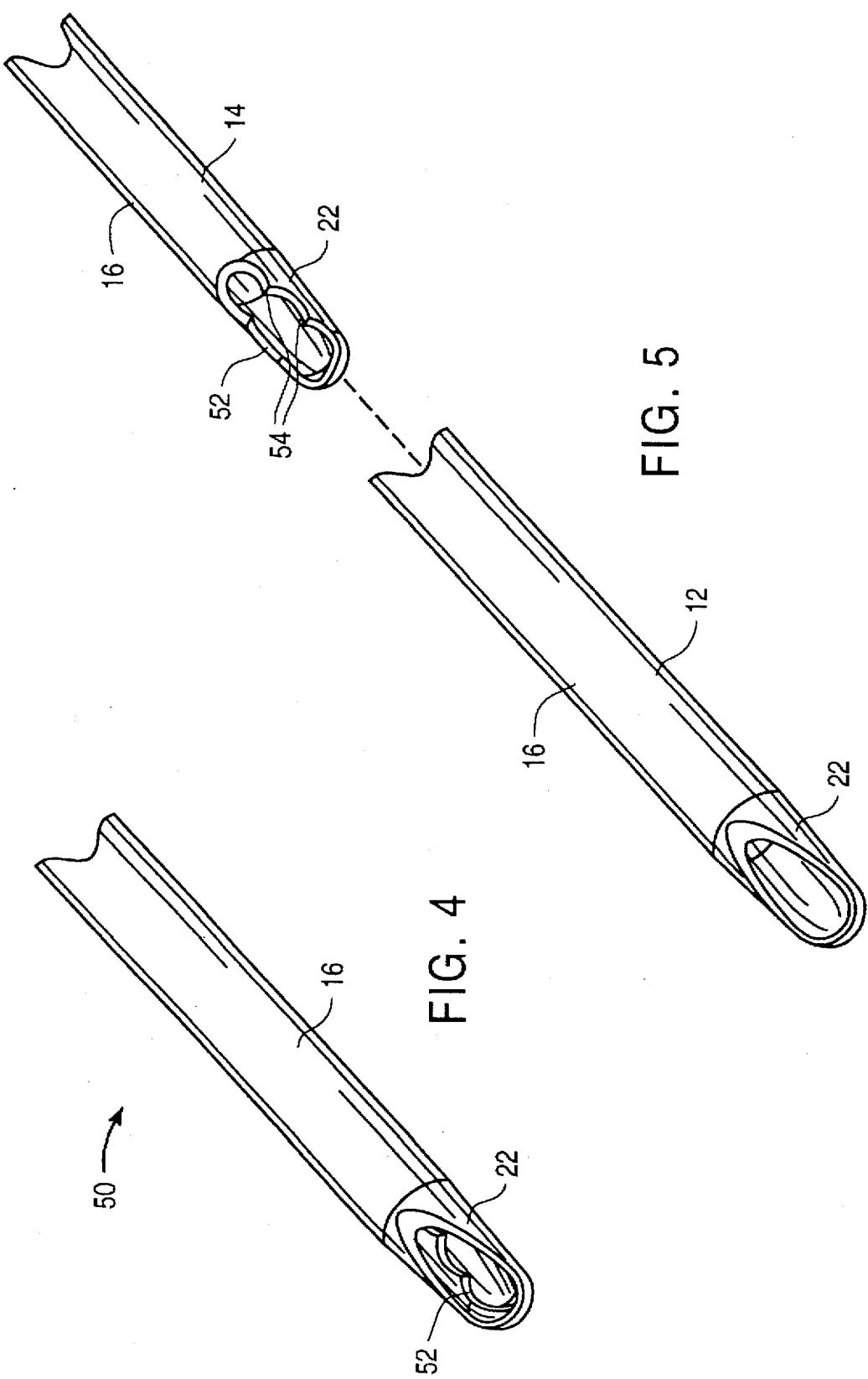

SURGICAL TUBULAR CUTTER HAVING A TAPERING CUTTING CHAMBER

CROSS REFERENCE TO RELATED APPLICATIONS

This application is a continuation-in-part of U.S. Provisional patent application Ser. No. 60/029,537, filed Nov. 1, 1996, the full disclosure of which is incorporated herein by reference.

BACKGROUND OF THE INVENTION

1. Field of the Invention

This invention relates generally to surgical Devices, and in particular, provides a tubular surgical cutter having a tapering cutting chamber to help ensure that tissues which are severed by the cutter can be aspirated without clogging.

Arthroscopic and endoscopic surgical techniques often involve manipulating a cutting probe through a small incision or body orifice. For example, arthroscopic knee surgery typically involves manually positioning the distal end of a probe against a tissue to be cut, typically against a meniscus in the knee joint. The piece of meniscus that is to be trimmed protrudes into an aperture formed in an outer tubular structure of the probe. An inner tubular structure rotates within this outer tube. The inner tube includes a chopping edge which sweeps by the outer aperture. Hence, the meniscus (or any other hard or soft tissues which protrude into the aperture) is sheared between the chopping edge of the inner tube and the edge of the aperture on the outer tube.

More recently, the use of similar tubular surgical cutting structures has been proposed for removal of tissues from internal surgical sites, particularly during transcervical resection of the endometrium, transurethral prostatic treatments, laparoscopic removal of thoracic tissues, and the like. U.S. patent application Ser. No. 08/542,289, filed Oct. 12, 1995, the full disclosure of which is incorporated herein by reference, describes an exemplary tissue resection device having an electrosurgical cutting member and a chopping mechanism formed from cooperating tubular cutters. In use, this exemplary tissue resection probe removes axial strips of tissue from an internal body cavity, and chops those strips of tissue into fragments with the chopping mechanism to facilitate their evacuation. Co-pending U.S. patent application Ser. No. 08/705,229, filed Aug. 29, 1996, (Attorney Docket No. 16944-001210), the full disclosure of which is also incorporated herein by reference, describes a similar probe having a plurality of morcellating rollers disposed along the cutting wire to decrease the size of tissues severed from the surgical site, thereby enhancing the amount of tissue which can be effectively removed from the surgical site for a given chopping mechanism size.

These known tubular surgical cutters have typically been formed as substantially cylindrical structures. While flat, hemispherical, or conical distal tips have been disposed at the distal ends of the cylindrical cutter members, the cutting apertures typically extend proximally well beyond these distal end shapes, and along the cylindrical cutter body. This arrangement facilitates manipulating the cutter laterally against the tissues to be removed. This lateral cutting motion is particularly effective when combined with a distally oriented viewing scope to allow the attending physician to direct and monitor the tissue removal.

While these known tubular surgical cutter systems have proved highly advantageous for removal of both hard and soft tissues, work in connection with the present invention has found that still further improvements could be beneficial. In particular, clogging of known tubular surgical cutters can be problematic, particularly when soft tissues are being removed. Generally, it is desirable to enhance the speed of tissue removal by providing a large aperture and a substantial aspiration flow proximally through the lumen of the cutting tubes. Unfortunately, this can lead to entrainment of excessively large tissue fragments within the aspiration lumen adjacent the cutting aperture. When excessively large tissue fragments are severed within this "cutting chamber", they will often be wedged in place even after being severed, blocking aspiration flow and preventing entrainment of additional tissue fragments. While it is possible to avoid such excessive tissue fragments by reducing the aperture and aspiration flow, this will also decrease the amount of tissue which can be removed for a given cutter size. Alternatively, increasing tubular surgical cutter diameters tends to increase trauma to the surrounding tissues, and decreases accuracy, control, and the ability to image the tissue removal procedure within the internal surgical site.

In light of the above, it would be desirable to provide improved tubular surgical cutters and methods for their use and fabrication which would reduce the likelihood that severed tissue would clog the probe. It would further be desirable if such enhanced cutter structures and methods could be easily combined with known arthroscopic, endoscopic, and resection probes, particularly if these improved cutter structures did not significantly increase the probe costs.

2. Description of the Background Art

U.S. Pat. No. 4,850,354 describes a surgical cutting instrument in which an outer tube has first and second cutting edges which define a corner, one of the cutting edges optionally being disposed along a distal conical section and the other being disposed along a proximal cylindrical section of the cutting tube.

U.S. Pat. No. 4,646,738 describes a rotary surgical tool in which an aperture on a cylindrical outer tubular member gives the tool a sloping profile. U.S. Pat. Nos. 5,217,479, 5,364,395, 5,269,798, 5,160,318, and 5,437,630 describe similar structures. U.S. Pat. Nos. 5,383,884 and 1,493,240 are also relevant.

SUMMARY OF THE INVENTION

The present invention provides tubular surgical cutters generally having conical or other tapering cutting chamber shapes along substantially the entire length of their cutting apertures. Advantageously, tissues which are drawn into such a conical chamber and severed from the adjacent tissue are quite easily drawn proximally by an aspiration flow, substantially reducing the likelihood that the severed fragments will clog the cutter mechanism. This simple adaptation of existing tubular cutters allows relatively aggressive aperture sizes and high aspiration rates to be applied, maximizing the amount of tissue which can be removed from an internal surgical site for a given cutter size. In some embodiments, an inner cutting tube having an orifice which is smaller than that of the outer cutting tube limits the size of tissue fragments entrained within the cutting chamber, further reducing the possibility that those fragments will clog the aspiration lumen and interrupt the tissue removal process.

In a first aspect, the present invention provides a tubular surgical cutter comprising a tubular body having a proximal end, a distal end, and a lumen therebetween. An outer tip extends distally from the distal end of the tube, and has an aperture and an inner surface bordering a chamber. The chamber is in communication with the lumen of the tube and the aperture. An inner tip is rotatably disposed within the chamber of the outer tip, and has an inner surface bordering a chamber and one or more apertures which cooperate with the aperture of the outer tip to sever tissues which protrude into the chamber when the inner tip rotates. The chamber of the inner tip receives the tissue along an axial cutting zone when the inner and outer apertures align. A cross-sectional radius of the chamber of either the inner tip or the outer tip decreases distally substantially throughout the axial cutting zone.

Typically, cross-sectional radii defined by the inner surface of both the inner tip and the outer tip will decrease distally substantially throughout the axial cutting zone, the cutting chambers typically comprising cones which are coaxial with the lumen of the tube. To further aid proximal aspiration of the severed tissue fragments, an inner tubular member generally extends proximally from the inner tip, the inner tube having an inner lumen with a cross-section which is larger than that of the inner chamber adjacent the cutting zone.

In another aspect, the present invention provides a tubular surgical cutter comprising an outer member which includes a tubular body and a tapered tip. The tube has a proximal end, a distal end, and a lumen extending therebetween, while the tapered tip extends distally from the distal end of the tube, and includes an aperture and an inner surface bordering a chamber. The chamber tapers substantially continuously from a large proximal radius to a small distal radius. The chamber is in communication with the lumen of the tube and with the aperture. An inner member is rotatably disposed within the lumen and the chamber of the outer member. The inner member comprises a tubular body having a proximal and distal end with a lumen therebetween. A tapered tip again extends distally from the distal end of the tube, the tip having an aperture and an inner surface bordering a chamber which tapers substantially continuously from a large proximal radius to a small distal radius. The chamber is in communication with the lumen of the tube and the aperture. The apertures of the outer member and the inner member cooperate to sever tissues along an axial cutting zone when the inner member rotates. The large radius of the tapered inner and outer tips are disposed proximally of the axial cutting zone to prevent the severed tissue from clogging the tube when the severed tissue is aspirated proximally.

In another aspect, the present invention provides a tubular surgical cutter comprising an outer tube having a proximal end, a distal end, and a lumen therebetween. An outer tip extends distally from the distal end of the outer tube, the outer tip having an aperture and an inner surface bordering a chamber. The chamber is in communication with the lumen of the outer tube and the aperture. An inner tip is rotatably disposed within the chamber of the outer tip, the inner tip having an inner surface bordering a chamber and a aperture which cooperates with the aperture of the outer tip to sever tissues which protrude into the chamber when the inner tip rotates. The chamber of the inner tip receives the tissues along an axial cutting zone when the inner and outer apertures align, and the aperture of the inner tip is smaller than the aperture of the outer tip to avoid severing large tissue fragments which would clog the lumen of the inner tube.

In yet another aspect, the present invention provides a method for fabricating a clog-resistant tubular surgical cutter, the method comprising fabricating a first tubular member with a first tapering region near a distal end. The first tapering region decreases in radius distally from a cylindrical region. A second tubular member is fabricated with a second tapering region near a distal end, the second tapering region decreasing in radius distally from a cylindrical region. The second tubular member is rotatably mounted within the first tubular member, so that the first tapering region aligns axially with the second tapering region. Apertures are formed through the first and second tapering regions distally of the cylindrical region for severing tissues which protrude through the apertures when the second tubular member rotates.

In yet another aspect, the present invention provides a method for severing and removing tissues from an internal surgical site, the method comprising protruding the tissue through an aperture into a chamber. The chamber tapers substantially continuously along the aperture from a large proximal radius to a small distal radius. The protruding tissues are severed between the aperture and a cooperating cutting edge, and the severed tissues are aspirated proximally from adjacent the small radius and past the large radius to avoid clogging.

BRIEF DESCRIPTION OF THE DRAWINGS

FIGS. 4 and 5 illustrate an alternative embodiment of a tubular surgical cutter according to the principles of the present invention.

DETAILED DESCRIPTION OF THE SPECIFIC EMBODIMENTS

The present invention will find applications in a wide variety of minimally invasive surgical procedures for the severing and/or removal of tissues from an internal surgical site. The tubular surgical cutters and methods of the present invention will find use in arthroscopy, laparoscopy, endoscopy, and hysteroscopy, for the severing and/or removal of tissues of the joints, the internal body organs, and the linings of the body cavities for a wide variety of minimally invasive surgical therapies. The tubular surgical cutters of the present invention can be used to sever tissues directly from these internal surgical sites, or may alternatively be used to morcellate and evacuate tissues which have been severed from the adjacent structures using an electrosurgical cutting/coagulation wire as described in co-pending U.S. patent application Ser. No. 08/542,289, filed Oct. 12, 1995 (Attorney Docket No. 16944-000130), previously incorporated herein by reference. Similarly, even where tissues to be removed have been substantially "vaporized" by application of relatively high electrosurgical currents, the present tubular surgical cutters can be used to remove a wide variety of debris fragment sizes released by such vaporization, as can be understood with reference to U.S. patent application Ser. No. 08/732,004, filed Oct. 16, 1996, (Attorney Docket No. 16944-000170), the full disclosure of which is also incorporated herein by reference. The methods and devices of the present invention will find their most immediate application for the morcellation and removal of endometrial tissues from the uterus.

Figure 1:
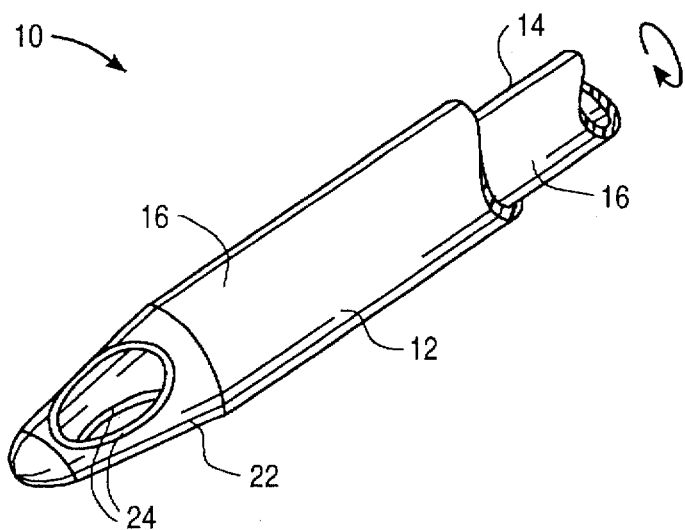
FIG. 1 is a perspective view of a tubular surgical cutter having a conical cutting chamber, according to the principles of the present invention.
Figure 2:
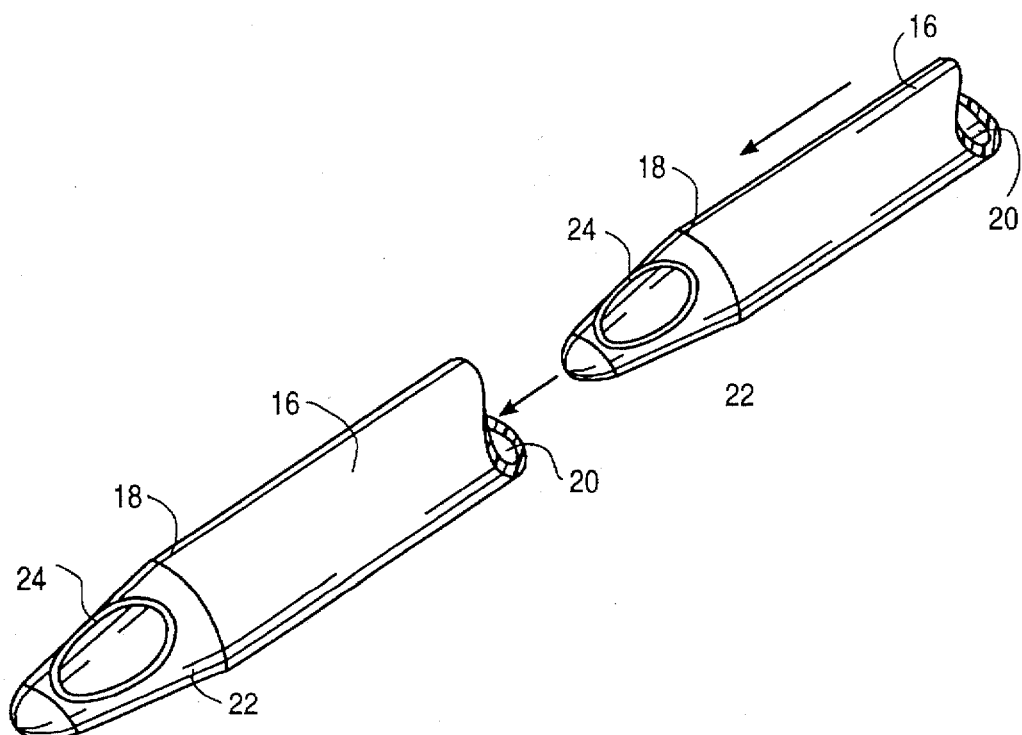
FIG. 2 is an exploded drawing of the tubular surgical cutter of FIG. 1, showing the conical cutting chamber shapes of both the inner and outer tubular members.

Referring now to FIGS. 1 and 2, a tubular surgical cutter 10 comprises an outer member 12 and an inner member 14. Each of the members generally includes a cylindrical tubular body 16 having a proximal end (not shown), a distal end 18, and a lumen 20 extending therebetween. A tapered tip 22 extends distally from each of the tubular bodies, and an aperture 24 is cut through each distal tip. By rotating the inner tubular member 14 within outer tubular member 12, the apertures will align to allow tissues to protrude into the tapering tips, and will thereafter slide past each other to sever those tissues, leaving the severed fragment within the inner tubular member for aspiration proximally through tubular surgical cutter 10. Optionally, two or more apertures may be provided on the inner member. However, this will impose additional features on the inner surface of the inner member which may retain the tissue fragments in the cutting chamber, thereby clogging the cutter.

In a particularly advantageous aspect of the present invention, the distal tapered tips 22 extend proximally of the apertures 24, so that the entire aperture is disposed distally of the cylindrical tubular bodies 16. Preferably, the entire distal tip tapers continuously from a relatively large cross-section adjacent tubular body 16 to a small cross-section adjacent the distal most portion of aperture 24. This geometry helps ensure that the tissue fragments will be free to move proximally through the lumen of the tubular surgical cutter. In other words, even if the tissue protrudes into the apertures to entirely fill the cross-section at any point axially along the aperture, the tissue fragments will still move proximally with relative ease, as the cross-section of the aspiration path increases in size as soon as the tissue fragments begins to move proximally.

Figure 3:
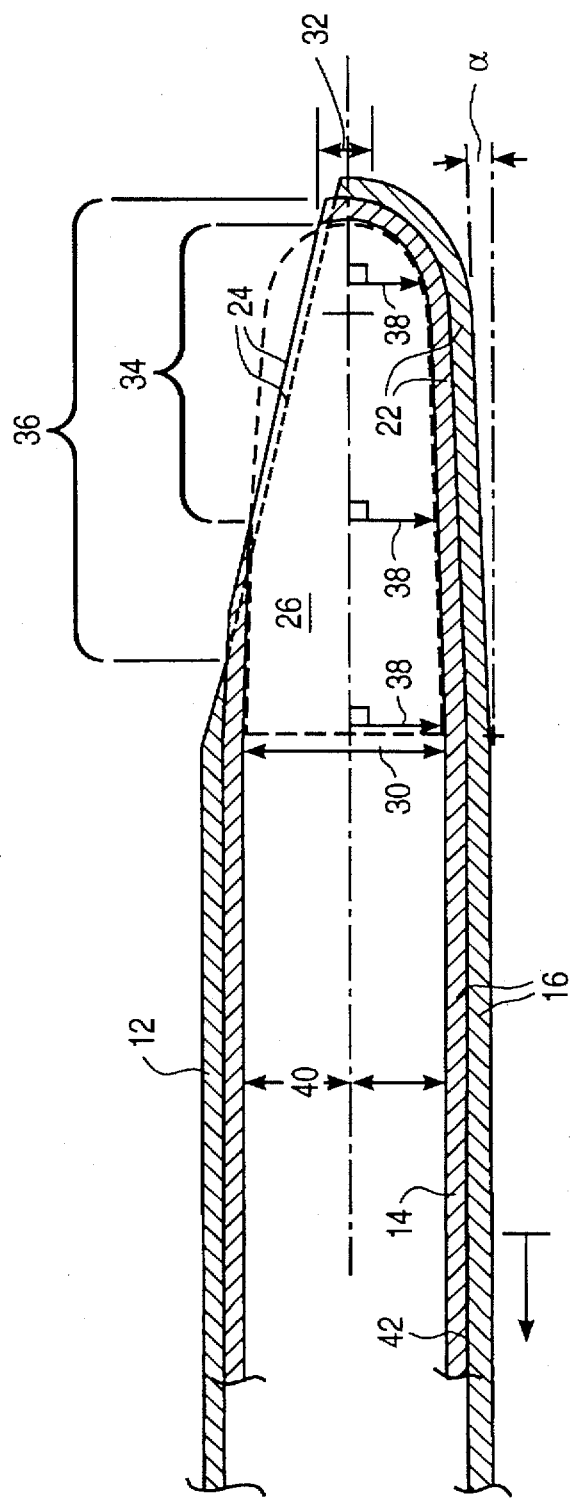
FIG. 3 is a cross-sectional view through both the inner and outer tubular members of the tubular surgical cutter of FIG. 1.

Referring now to FIG. 3, the tapered shape of distal tip 22 defines a tapered chamber 26 within the inner tubular member as shown. A similar tapered chamber is defined by the inner surface of the distal tip of the outer tubular member. Theoretically, the shape of the inner chamber may limit the size of tissue fragments which will be accepted by the tubular surgical cutter, while the size and shape of the outer chamber may determine where the tissue fragment will be severed, as tissue severing will be provided by a shearing action between the adjacent apertures. While some of the benefits of the present invention may be provided where only the inner or outer chamber is tapered, exemplary embodiments will include distal tips having tapered chambers for both the inner and outer members.

As described above, distal tips 22 will preferably comprise conical surfaces having continuous tapers adjacent the apertures 24. Advantageously, only a relatively shallow taper angle $\alpha$ is required, so that distally oriented optical scopes will still have a good field of view for directing the severing and removal of tissues. Preferably, taper angle $\alpha$ is between about 2° and 25°. In some embodiments, it may be desirable to have a varying taper angle with a parabolic, elliptical, or other continuously tapering shape.

In the exemplary embodiment shown, the inner surface of the inner tubular member defines a chamber which tapers from a relatively large cross-section 30 adjacent the cylindrical tubular bodies, to a much smaller cross-section 32 at the distal end of the effective aperture. The effective aperture is substantially defined by the inner tubular member 14, so that only tissue which is disposed adjacent a tissue cutting zone 34 will protrude into the inner chamber, and will be severed when the inner tubular member rotates. The aperture to the outer tubular member defines a significantly larger open zone 36. By limiting the size of the cutting zone with the inner tubular member, only smaller tissue fragments are admitted into the chamber to be cut. This has the drawback of making the cutter less aggressive, potentially slowing down the rate of tissue severing and removal. Nonetheless, such a cutter can enhance the overall speed of a tissue removal procedure by eliminating or reducing clogging. The small axial cutting zone does decrease the ability of the tubular surgical cutter to grab and hold previously severed tissues when previously severed tissue is to be morcellated and extracted.

Generally, the inner surface of at least the outer tip will comprise a surface of revolution to allow the inner tip to rotate therein. Typically, both the inner and outer chambers will comprise bodies of revolution. As a result of the tapering shape of the chambers within the inner and outer tips, the radii 38 defining these bodies of revolution will decrease distally throughout the axial cutting zone 34. Typically, these radii will decrease from adjacent the tubular bodies throughout the distal tip, tubular bodies 16 typically providing an aspiration lumen having a cross-section with a radius 40 which is larger than the radius throughout the cutting zone. This helps ensure that tissues which move proximally from the cutting zone will continue to move proximally without blocking or clogging the tubular surgical cutter. Often times, an increased gap 42 will be provided between the inner and outer tubular members to reduce friction, ideally without decreasing the aspiration path lumen as the tissue fragments move proximally.

It should be recognized that the smaller aperture provided on the inner tubular member relative to the outer tubular member can reduce clogging of tubular surgical cutters which do not include the conical cutting chamber of the preferred embodiment of the present invention. The inner aperture may be smaller in open area, axial length, or transverse width than the aperture of the outer tubular member, ideally being smaller in all three dimensions. Surprisingly, this may result in tubular surgical cutters in which the inner member protrudes through the aperture of the outer member when viewed from the side, even when the apertures are aligned.

In a preferred method for making tubular surgical cutter 10, the inner and outer tubular members are formed with a closed tapering distal tip. Optionally, tapering tips may be welded on tubular bodies, or a distal end can be welded or formed on the distal end of a cylindrical tubular body, and the distal portion of the cylindrical body drawn axially to taper its cross-section. Regardless, the apertures can then be cut (which here includes grinding) through the tapered distal portion, leaving the cylindrical body substantially intact. Ideally, the inner and outer apertures are formed separately to provide a larger outer aperture, as described above. Inner tubular member 14 is then rotatably mounted within outer tubular member 12, as is generally known in the art.

Referring now to FIGS. 4 and 5, an alternative tubular surgical cutter 50 includes tapering cutting chambers and a smaller aperture on the inner member, as described above. Additionally, inner member 14 here has a scalloped aperture 52 to provide one or more gripping points 54. These gripping points help to hold tissue in position for severing, and thereby provide a more aggressive cutting action. The points also prevent the tissue from slipping axially from between the cooperating aperture edges. Such points may be produced by a triangular sawtooth (rather than scalloped) aperture, or by a variety of alternative shapes.

Although the exemplary embodiments of the tubular cutters of the present invention have been described in some detail, by way of illustration and example, a variety of modifications and changes will be obvious to those of skill in the art. Therefore, the scope of the present invention is limited solely by the appended claims.

What is claimed is:

1. A tubular surgical cutter comprising:
   a tubular body having a proximal end, a distal end, and a lumen therebetween;
   an outer tip extending distally from the distal end of the tubular body, the outer tip having an aperture and an inner surface bordering a chamber, the chamber being in communication with the lumen of the tube and the aperture; and
   an inner tip rotatably disposed within the chamber of the outer tip, the inner tip having an inner surface bordering a chamber and an aperture which cooperates with the aperture of the outer tip to sever tissues which protrude into the chamber when the inner tip rotates;
   wherein the chamber of the inner tip receives the tissues along an axial cutting zone when the inner and outer apertures align, wherein a proximal end of one of the apertures defines a proximal end of the axial cutting zone, wherein a distal end of one of the apertures defines a distal end of the axial cutting zone, and wherein at least one of the chambers has a radius which decreases distally substantially throughout the axial cutting zone.

2. A tubular cutter as claimed in claim 1, wherein cross-sectional radii defined by the inner surface of the inner tip and the inner surface of the outer tip decrease distally substantially throughout the axial cutting zone.

3. A tubular cutter as claimed in claim 1, wherein the at least one chamber comprises a cone which is substantially coaxial with the lumen of the tubular body.

4. A tubular surgical cutter comprising:
   a tubular body having a proximal end, a distal end, and a lumen therebetween;
   an outer tip extending distally from the distal end of the tube, the outer tip having an aperture and an inner surface bordering a chamber, the chamber being in communication with the lumen of the tube and the aperture;
   an inner tip rotatably disposed within the chamber of the outer tip, the inner tip having an inner surface bordering a chamber and an aperture which cooperates with the aperture of the outer tip to sever tissues which protrude into the chamber when the inner tip rotates;
   wherein the chamber of the inner tip receives the tissues along an axial cutting zone when the inner and outer apertures align, wherein a proximal end of one of the apertures defines a proximal end of the axial cutting zone, wherein a distal end of one of the apertures defines a distal end of the axial cutting zone, and wherein at least one of the chambers has a radius which decreases distally substantially throughout the axial cutting zone; and
   an inner tubular body extending proximally from the inner tip, the inner tube having an inner lumen with a cross-section which is larger than the cross-section of the chamber of the inner tip throughout the axial cutting zone.

5. A tubular cutter as claimed in claim 1, wherein the aperture of the inner tip is smaller than the aperture of the outer tip.

6. A tubular surgical cutter comprising:
   an outer member comprising a tubular body having a proximal end, a distal end, a lumen extending therebetween, and a tapered tip extending distally from the distal end of the tube, the tip having an aperture and an inner surface bordering a chamber which tapers continuously from a large proximal radius to a small distal radius, the chamber being in communication with the lumen of the tube and the aperture; and
   an inner member rotatably disposed within the lumen and the chamber of the outer member, the inner member comprising a tube having a proximal end, a distal end, and a lumen therebetween, and a tapered tip extending distally from the distal end of the tube, the tip having an aperture and an inner surface bordering a chamber which tapers continuously from a large proximal radius to a small distal radius, the chamber being in communication with the lumen of the tube and the aperture;
   wherein the apertures of the outer member and the inner member cooperate to sever tissues along an axial cutting zone when the inner member rotates, and wherein the large radii of the tapered inner and outer tips are disposed proximally of the apertures and the small radii are distal of the apertures so that the chambers taper throughout the apertures to prevent the severed tissues from clogging the inner tube when the severed tissue is aspirated proximally.

7. A method for fabricating a clog-resistant tubular surgical cutter, the method comprising:
   fabricating a first tubular member with a first tapering region near a distal end, the first tapering region decreasing in radius distally from a cylindrical region;
   fabricating a second tubular member with a second tapering region near a distal end, the second tapering region decreasing in radius distally from a cylindrical region;
   rotatably mounting the second tubular member within the first tubular member so that the first tapering region aligns axially with the second tapering region, and
   forming apertures through the first and second tapering regions distally of the cylindrical regions for severing tissues which protrude through the apertures when the second tubular member rotates, wherein the apertures are formed so that proximal ends of the apertures are disposed along the tapering region.

8. A method as claimed in claim 7, wherein the aperture forming step comprises cutting an aperture in the second tubular member to a second aperture size and separately cutting an aperture in the first tubular member to a first aperture size which is larger than the second aperture size so that the second tubular member protrudes through the first aperture when the first and second apertures are aligned.

9. A method for severing and removing tissues from an internal surgical site, the method comprising:
   protruding the tissues through an aperture into a chamber, wherein the chamber tapers substantially continuously throughout the aperture from a large proximal radius to a small distal radius;
   severing the protruding tissues between the aperture and a cooperating cutting edge; and
   aspirating the severed tissue proximally adjacent the small radius and past the large radius to avoid clogging.

10. A method as claimed in claim 9, wherein the severed tissue is aspirated proximally through a lumen which has a larger cross-section than the chamber.

11. A tubular surgical cutter comprising: an outer tubular body having a proximal end, a distal end and a lumen therebetween;
   an inner tubular body having a proximal end, a distal end and a lumen therebetween, the inner tubular body disposed within the lumen of the outer tubular body;

an outer tip extending from the distal end of the outer tubular body, the outer tip having an aperture with a proximal end and an inner surface;

an outer chamber defined by the inner surface of the outer tip, the outer chamber being in communication with the lumen of the outer tubular body and the outer aperture;

an inner tip extending from the distal end of the inner tubular body and rotatably disposed within the outer chamber, the inner tip having an inner surface and an aperture bordered by a cutting edge;

an inner chamber defined by the inner surface of the inner tip, the inner chamber being in communication with the lumen of the inner tubular body and the inner aperture; and an axial cutting zone defined by the entire alignment of the inner and outer apertures, the inner chamber having a cross-section, throughout the cutting zone, which is smaller than the cross-section of the inner lumen, wherein a radius of the inner chamber decreases distally substantially continuously throughout the cutting zone.

12. A tubular cutter as claimed in claim 11, wherein the aperture of the inner tip is smaller than the aperture of the outer tip.

13. A tubular cutter as claimed in claim 11, wherein the cutting edge is scalloped, wherein the scalloped edge defines one or more protruding points for grasping tissue.

14. A tubular surgical cutter comprising:

an outer member comprising:
    a tubular body having a distal end, a proximal end, and a lumen therebetween; and
    a tapered tip extending distally from the tubular body, the tapered tip having an aperture, the aperture having a proximal end and a distal end and defining an aperture axial length therebetween;

an inner member rotatably disposed within the tapered tip, the inner member having a cutting edge; and an inner chamber defined by a path swept by the cutting edge of the inner member when the inner member rotates, wherein the inner chamber tapers inwardly and distally substantially continuously throughout the aperture length.

15. A tubular surgical cutter as claimed in claim 1, wherein the at least one of the chambers has a radius which decreases distally continuously throughout the axial cutting zone.

* * * * *